United States Patent [19]

Johnson et al.

[11] Patent Number: 5,144,012

[45] Date of Patent: Sep. 1, 1992

[54] CYTOTOXIC DRUG CONJUGATES

[75] Inventors: David A. Johnson, Carmel; Bennett C. Laguzza; William L. Scott, both of Indianapolis, all of Ind.

[73] Assignee: Eli Lilly and Company, Indianapolis, Ind.

[21] Appl. No.: 656,343

[22] Filed: Feb. 15, 1991

Related U.S. Application Data

[62] Division of Ser. No. 229,941, Aug. 8, 1988, Pat. No. 5,028,697.

[51] Int. Cl.$^5$ .................. C07K 17/06; C07K 17/14; C07K 15/28
[52] U.S. Cl. .................. 530/391.9; 530/391.1; 530/391.5; 530/409; 530/410; 530/807; 435/188
[58] Field of Search .................. 530/409, 391.1, 391.5, 530/391.9, 410, 807; 435/188

[56] References Cited

U.S. PATENT DOCUMENTS 4,631,190 12/1986 Shen et al. .................. 424/85.91
4,671,958 6/1987 Rodwell et al. .................. 424/85.91

FOREIGN PATENT DOCUMENTS 0056322 7/1982 European Pat. Off. .
0088695 9/1983 European Pat. Off. .
0124502 7/1984 European Pat. Off. .
0243929 11/1987 European Pat. Off. .
00253202 1/1988 European Pat. Off. .
WO/87/6837 11/1987 Int'l Pat. Institute .
2137210A 10/1984 United Kingdom .

OTHER PUBLICATIONS

Pietersz (1990) Bioconjugate Chemistry 1(2):89–95.
Kennedy et al. (1976) Clin. Chim. Aeta 70: 1–31.
Blair, et al., *Jour. of Immunological Methods*, vol. 59, pp. 129–143 (1983).
King et al., *Biochem.* 25, 5774–79 (1986).
Ghose et al., *Methods Enzymology* 93, 280–333 (1983).
Ghose et al., *CRC Critical Rev. in Therapeutic Drug Carrier Systems* 3, pp. 263–359 (1987).
Shen et al., *Biochem. Biophys. Res. Comm.* 102, 1048–1054 (1981).
Bumol et al., FASEB 69th Annual Meeting, Abstract 8484 (1985).
Bumol et al., AACR Proceedings, vol. 24, Abstract 1410 (1984).
Bumol et al., *J. Cell Biochem.*, Supp. 9A, Abstract 0124 (1985).
Kanellos et al., *J. Nat. Cancer Institute* 75, 319–332 (1985).
Lopes et al., *Clinical Immunology* (Proc. First IUIS Conference, Jul. 6–11, 1986) pp. 303–307 published 1987.
Oi et al., *Biotech 4* (3):214–221 (1986).
Umemoto et al., *Int. J. Cancer* 43:677–684 (1989).

*Primary Examiner*—Christine M. Nucker
*Assistant Examiner*—Kay K. Kim
*Attorney, Agent, or Firm*—John E. Parrish; Leroy Whitaker

[57] ABSTRACT

Conjugates of antibodies and cytotoxic methotrexate drugs make use of liners between the drug and antibody which are simple organic groups, wherein the link to the antibody is an acyl group and the link to the drug is an alkylidene hydrazide.

5 Claims, No Drawings

CYTOTOXIC DRUG CONJUGATES

This application is a division of application Ser. No. 07/229,941, filed Aug. 8, 1988 now U.S. Pat. No. 5,028,697.

FIELD OF THE INVENTION

The present invention belongs to the fields of organic chemistry, immunology, and pharmaceutical chemistry, and provides cytotoxic drug conjugates useful for the targeted administration of cytotoxic drugs to patients in need of such treatment. Targeting of the drug conjugates is obtained by the use of antibodies which recognize an antigen associated with the cell to be treated with the cytotoxic drug, and which antibodies thereby carry the cytotoxic drug to the cell. Intermediates used in the synthesis of the conjugates are also provided.

BACKGROUND OF THE INVENTION

As long ago as 1900, Ehrlich proposed that drugs might be guided to the target organ by attaching the drugs to substances which would seek that target organ. The technology to follow up on Ehrlich's suggestion did not exist until monoclonal antibody technology began to appear in the 1970's. For some years now, publications on the targeting of drugs with the aid of antibodies have been regularly appearing. However as yet, no antibody-conjugated drug is approved for therapeutic use. Chemists and immunologists continue to experiment, seeking a method of making antibody-drug conjugates which will transport the drug reliably to the target organ and release it at the proper time. The present invention provides a series of methotrexate drug conjugates linked to antibodies by means of a linker system which appears to provide particularly good release of the drug.

SUMMARY OF THE INVENTION

The present invention provides a cytotoxic drug conjugate of the formula $$Ab[CO-X=N-HN-M]_m \quad \text{I}$$

wherein m is an integer from 1 to about 10;

Ab is a physiologically-acceptable antibody or antigen-recognizing fragment thereof, which recognizes an antigen associated with an undesirable cell;

X is a linker of the formula $$-(CH_2)_n-\overset{R}{\underset{|}{C}}= \quad \text{II}$$

$$-(CH_2)_n-Ar-CH= \quad \text{III}$$

$$-(CH_2)_n-CO-NH-(CH_2)_n-CH=, \text{ or} \quad \text{IV}$$

$$-\overset{R^1}{\underset{|}{CH}}-(CH_2)_n-NH-CO-R^2-CH=; \quad \text{V}$$

R is hydrogen, phenyl, or phenyl substituted with one or two nitro, halogen, cyano or trifluoromethyl groups;
Ar is

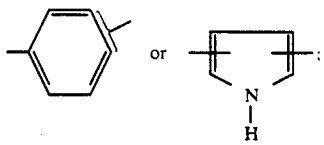

$R^1$ is hydrogen, amino, amino-$C_1$-$C_4$ alkyl, hydroxy-$C_1$-$C_4$ alkyl, or guanidino-$C_1$-$C_4$ alkyl;
$R^2$ is $(CH_2)_{n'}$

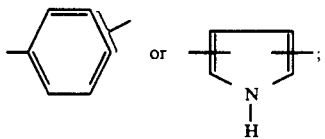

n is an integer from 0 to 5;
M is a methotrexate drug of the formula

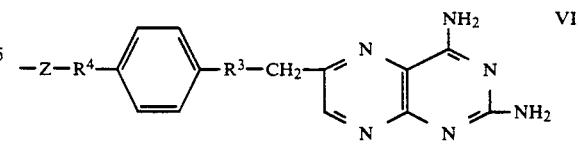

$R^3$ is

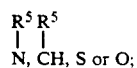

N, CH, S or O;

$R^4$ is CO, $SO_2$, CO—$(CH_2)_s$ or CO—NH;
$R^5$ is hydrogen or $C_1$-$C_3$ alkyl;
s is one or two;
Z is

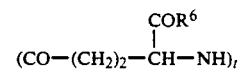

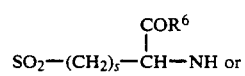

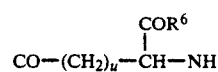

t is an integer from 1 to 6;
u is an integer from 1 to 22;
$R^6$ is hydroxy or a moiety which completes a physiologically-acceptable salt.

The invention also provides a series of derivatized antibodies of the formula $$Ab[CO-X=R^8]_m$$

wherein $R^8$ is O, $(OCH_3)_2$ or $(OCH_2CH_3)_2$, and X and m have the above-stated meanings.

The invention also provides a method of controlling the growth of an undesirable cell which comprises administering a conjugate of the invention parenterally to a patient, and pharmaceutical compositions comprising a conjugate of the invention dispersed in a parenterally-administrable medium.

DETAILED DESCRIPTION OF THE INVENTION

The present drug conjugates are composed of an antibody, a linker and a methotrexate drug in the hydrazide form. The desirable therapeutic properties of the conjugates are primarily obtained from the linker, which is so designed as to release the methotrexate drug from the antibody after the drug has been delivered to the vicinity of the target cell by the antibody. The three major components of the conjugates will be discussed individually, the synthesis of the conjugates will then be explained, and, finally, examples of the synthesis and biological testing of the conjugates will be shown.

The Antibody

The essential property of the antibody portion of the conjugates is its ability to recognize an antigen associated with an undesirable cell. It will be understood that the methotrexate drugs are highly cytotoxic to a wide variety of cells, and that those drugs exhibit their full potency when internalized into the target cell. Thus, the antibody is preferably chosen for its ability to recognize, bind to and be internalized by the cell which is to be killed or otherwise controlled with the methotrexate drug.

The source of the antibody is not critical to the present invention. It may be chosen from any class or subclass of immunoglobulin including IgG, IgA, IgM, IgE and IgD. Similarly, the species of origin is not critical so long as the antibody targets a cell where the effect of the methotrexate drug is useful.

In the present state of the art, monoclonal antibodies are most used in drug conjugates, and use of them is preferred in the present invention. However, polyclonal antibodies are not excluded. A newer type of antibody is the chimeric antibody, which is prepared in the laboratory by recombinant technology which permits expression of a modified DNA which encodes the antigen-binding region of any desired antibody, and also encodes any other desired amino acid sequences. Thus, chimeric antibodies of which one portion is derived from one species, and another portion is derived from another species may be obtained and used in the present invention.

The origin and nature of the antibody is not otherwise critical, so long as it targets the cell to be treated and is not, in itself, toxic to the patient. Those of ordinary skill can readily prepare conjugates with a candidate antibody and evaluate them. Some discussion of the method of evaluating antibodies and conjugates will be provided for convenience. First, the antibody should be produced by a hybridoma which is sufficiently stable to allow preparation of reasonable quantities of antibody. The antibody itself should be amenable to purification, and in particular should be sufficiently water-soluble to allow chemical manipulations at reasonable concentration.

Conjugates prepared with the candidate antibody are first evaluated for antigen-binding capacity. A modest reduction from the binding capacity of the free antibody is expected and acceptable. Then, the conjugate is tested to determine its in vitro cytotoxicity, against antigen positive cells. An effective conjugate can have cytotoxicity somewhat less than the free drug in the same assay. A conjugate which is accepted in the first two tests is then evaluated in a nude mouse human tumor xenograft model, as taught by Johnson and Laguzza, *Cancer Res.* 47, 3118-22 (1987). The candidate conjugate should be tested in nude mice against the free drug, a mixture of free drug and free antibody, and a conjugate with a non-targeting immunoglobulin, and should exhibit improved potency or safety over all. Dose ranging studies should be carried out in the xenograft model.

Conjugates which are potent in the xenograft model are submitted to tests in animals which are known to express the antigen of interest in a pattern similar to that seen in humans. If the conjugate produces a significant degree of binding to the antigen in such tests, and if it is reasonably free of toxicity at doses predicted by the xenograft model to be therapeutic, the candidate conjugate can be considered to have therapeutic potential.

Many presently known antibodies are available for use in the present invention. The preferred specific antibody is L/1C2, which is produced by a hybridoma on deposit in the American Type Culture Collection, Rockville, Md., as HB9682.

Antibody 5E9C11, produced by an ATCC hybridoma, HB21, recognizes transferrin receptor, which is expressed by many tumors. An antibody called B72.3, available from the National Cancer Institute, recognizes antigens expressed by both breast and colon carcinoma.

Two interesting antibodies with reactivities against non-tumor antigens are OKT3 and OKT4, which bind to peripheral T-cells and human T-helper cells, respectively. They are produced by hybridomas on deposit in the ATCC as CRL8001 and CRL8002, respectively.

Additional sources of antibodies useful for various therapeutic purposes are the following. Antihuman lymphocyte and monocyte antibodies, useful for immune modulation and tumor therapy, are produced by ATCC cultures HB2, HB22, HB44, HB78 and HB136. An antitransferrin receptor antibody, useful for tumor therapy, is produced by ATCC culture HB84. ATCC culture HB8059 produces an antibody against colorectal carcinoma monosialoganglioside, and culture HB8136 produces an antibody against mature human T-cell surface antigen, useful for immune modulation and T-cell leukemia therapy.

Further candidate antibodies are readily located by those of skill in the art. A particularly useful source of information about readily available antibodies is Linscott's Directory of Immunological and Biological Reagents, published by Linscott's Directory, 40 Glen Drive, Mill Valley, Calif. 94941. The 1984 edition lists more than 60 tumor-associated monoclonal antibodies, and at least one commercial source for each.

It will be understood that a variety of undesirable cells may be treated with conjugates of the present invention. The methotrexate drugs are widely known to be active against the various types of cancer cells, and it is contemplated that cancer cells are among the preferred cells to be targeted by the present conjugates.

In particular, cells which support continued development of a malignancy, and cells of the immune system which control development of anti-tumor immunity are also contemplated. Specific types of cancer-related cells to be targeted include squamous carcinoma cells, adenocarcinoma cells, small cell carcinoma cells, glioma cells, melanoma cells, renal cell carcinoma cells, transitional cell carcinoma cells, sarcoma cells, cells of supporting tumor vasculature, and cells of lymphoid tumors such as leukemias and lymphomas.

However, the methotrexate drugs are also cytotoxic to many other types of cells. Thus, the conjugates can be used, by proper choice of the antibody, to kill or modify such undesirable cells as, for example, cells infected with virus particles, T cells infected with various harmful agents, and cells of the immune system which promote or control development of autoimmune diseases.

It will be understood that properly chosen fragments of antibodies have the same effect as the intact antibody. Thus, in the practice of this invention, antibody fragments, preferably F(ab')2 fragments, which recognize an antigen associated with the cell to be treated, may be just as useful as are intact antibodies.

The exact mechanism by which the linker group reacts with and attaches to the antibody is not shown in formula I, and is not perfectly known. The reaction presumably is an acylation, as is demonstrated below, and a number of locations on antibody molecules are subject to acylation. Most commonly, acylations of antibodies are thought to proceed on the free amino groups of lysine moieties. However, the acylation can also attack hydroxy groups, phenol groups, imidazole rings and perhaps other moieties.

Formula I indicates that from 1 to about 10 linker-drug moieties are attached to each molecule of antibody. Of course, the number of such moieties per antibody molecule is an average number because a given batch of conjugate will necessarily contain molecules having a range of ratios of drug-linker to antibody. The most efficient use of the expensive antibody is obtained, of course, when a number of molecules of drug are attached to each antibody molecule. However, the attachment of an excessive number of molecules of drug-linker moiety usually has an adverse effect on the antibody's ability to recognize and bind to its antigen, so a compromise value for m must be found. In general, the preferred value for m is from about 4 to about 10; another preferred value is from about 3 to about 8.

The Methotrexate Drug

The cytotoxic drug used in the present conjugates is methotrexate, aminopterin or a derivative thereof of formula VI, which compounds are collectively called methotrexate drugs in this document. The methotrexate drugs are used in the hydrazide form. The stereospecific forms of the various asymmetric centers of the drug are not indicated. Those of ordinary skill will understand that the stereochemistry of the drug may affect its activity, as is clearly explained in the art. The usual stereochemistry of the methotrexate drugs is preferably used in preparing intermediates for the present conjugates, but formula VI includes all stereochemical forms.

The bond between the methotrexate drug hydrazide and the linker is an alkylidene hydrazide bond. It will be understood, however, that the bond may exist in other forms in solution, particularly in physiological solution. The double bond can be opened, allowing functional groups or protons to bond to the nitrogen and carbon atoms. As a result, a hydroxy group or other oxygen-linked species may attach to one side of the former double bond, and amino-linked moieties may do so as well. Water can weakly bond to one of the atoms. A moiety of the antibody also can form a weak bond to one of the atoms, and more than one of such reactions may occur, forming mixtures. Such products are transitory, however, and throughout this document the conjugates will be described as in the alkylidene hydrazide form, because that is the general and stable form of them.

In formula VI, the term $C_1$–$C_3$ alkyl includes methyl, ethyl, propyl and isopropyl, preferably methyl or hydrogen.

The various groups which can vary in the drug of formula VI will be discussed individually, and some preferred definitions of each will be given. It will be understood that preferred methotrexate drug hydrazides are made up of the preferred constituent groups, and pharmaceutical chemists, having knowledge of the pertinent literature, can prepare any such drug hydrazide.

The group $R^3$ is a bridging group which can be sulfur, oxygen, amino or methylene, the latter two of which may be optionally substituted with $C_1$–$C_3$ alkyl. Typical such groups are amino, methylene, methylamino, propylamino, 1,1-propylene and 1,1-isobutylene. The preferred $R^3$ groups are amino and methylamino.

The group $R^4$ is a bridging group which may be carbonyl, sulfonyl, acetyl, propionyl or carboxamido. In the latter three instances, the carbonyl group is adjacent to the group Z. The most preferred $R^4$ group is carbonyl, and acetyl and propionyl are also preferred.

The group Z has an amino group at one end, which is attached to the group $R^4$, and has a carbonyl or sulfonyl group at the other end, which is attached to the =N—HN group. The Z group of formula VII is derived from glutamic acid and, when t is not 1, constitutes the residue of polyglutamic acid. The preferred Z group of formula VII, however, is that wherein t is 1.

The Z group of formula VIII terminates in a sulfonyl, and accordingly is the residue of the corresponding sulfonic acid. The group of formula VIII has one or two methylene groups, preferably two.

The Z group of formula IX is an amino acid of variable length, which may contain from 1 to 22 methylene groups. A preferred class of groups of formula IX contains from 1 to 10 methylene groups, more preferably from 3 to 8 methylene groups.

The most preferred Z groups are those of formula VII, wherein t is 1, and those of formula IX, wherein u is from 3 to 8.

In the groups of formula VII, VIII and IX, a carboxy group $R^6$ is present, in either free or salt form. The salts are formed with any moiety capable of forming a physiologically-acceptable salt of the carboxylic acid. Alkali metal and hydrohalide salts are particularly appropriate. Thus, the sodium, potassium and lithium salts, as well as the hydrochloride, hydrobromide and hydrofluoride salts, are particularly useful in the practice of the present invention. Other salts acceptable in pharmaceutical chemistry, however, are also useful. For example, amine salts such as triethylamine, triethanolamine, ethyldimethylamine and the like are useful, as are quaternary ammonium salts including tetraalkylammonium salts, (benzyl or phenyl)trialkylammonium salts and the like. Among ammonium salts, tetrabutylammonium, benzyltrimethylammonium, and tetramethylammonium are typical and preferred salts. Pharmaceutical chemists continually use salts of carboxylic acids, however, and the present salts, wherein $R^6$ is a salt-forming moiety, may be prepared with any base which forms a physiologically-acceptable salt.

The necessary intermediates from which to derive groups of formula VI are in the pharmaceutical chemical art, and those of ordinary skill in that art can obtain any of them. A useful review article on the synthesis of methotrexate drugs is Rahman and Chhabra, The Chemistry of Methotrexate and its Analogues, *Medicinal Res. Rev.* 8, No. 1, 95-155 (1988).

The Linker

The linker group X is an organic group which is bonded to the carbonyl at one end, and to the hydrazide at the other.

The linker group of formula II is an alkylene group, wherein the moiety $(CH_2)_n$ is, for example, methylene, ethylene, propylene, pentylene and the like.

The group R is hydrogen or phenyl, which may be substituted with one or two electron-withdrawing groups. Thus, the group R may be phenyl, 3-nitrophenyl, 2,4-dichlorophenyl, 3-bromo-5-fluorophenyl, 4-cyanophenyl, 3-trifluoromethylphenyl, 2-chloro-4-trifluoromethylphenyl, 3-nitro-4-trifluoromethylphenyl and the like. The term halogen is used in this document to refer to chloro, bromo and fluoro. Hydrogen is a preferred R group; unsubstituted phenyl is another preferred R group, and a third preferred R group is monosubstituted phenyl.

The group of formula III is an alkylaryl moiety wherein the bridging aryl group Ar is phenyl or pyrrolyl. A phenyl Ar group is linked at the meta or para position, preferably at the para position. The moiety $(CH_2)_n$ in the group of formula III is the same as the corresponding group in formula II; thus, when n is 0, the group is nothing more than a bond, or it may be an alkylene group as described above. It is preferred for n to be 0; it is also preferred for n to be 2-4.

The group of formula IV is an amide-bonded linker, which may contain one or two alkylene bridges. The alkylene groups, $(CH_2)_n$, in the group of formula IV are the same as those discussed above under the group of formula II. In the design of groups of formula IV, the two optional alkylene bridges may be considered independently—that is, n may be 0 in both instances, one may be 0 and the other may be an integer from 1 to 5, or both may be integers from 1 to 5. It is preferred that both of the groups $(CH_2)_n$ be alkylene groups wherein n is from 1 to 4, more preferably 2 or 3.

The group of formula V is a more complex amide-linked group, often incorporating an amino acid moiety. The group $(CH_2)_n$ is similar to the same group as discussed under formula II. The pendant group may be a $C_1$-$C_4$ alkyl group, substituted with amino, hydroxy or guanidino (NH—C(=NH)—NH$_2$). Thus, it includes groups such as aminomethyl, 2-aminoethyl, 4-aminobutyl, 2-hydroxyethyl, 3-hydroxypropyl, 4-hydroxybutyl, guanidinomethyl, 2-guanidinoethyl, and 4-guanidinobutyl, for example. $R^1$ may also be hydrogen or amino. Preferred $R^1$ groups are amino, hydroxymethyl, aminoalkyl, especially 4-aminobutyl, and guanidinoalkyl, especially 4-guanidinobutyl.

The group $R^2$ is a bond when n is 0, or may be an alkylene group of 1 to 5 carbon atoms, phenyl or pyrrolyl. A phenyl $R^3$ group is linked at the meta or para position. A $(CH_2)_n$ group is the same as the corresponding alkylene group described under the group of formula II, and may have the same values.

The most preferred linker groups of formulae II, III, IV and V are 4-benzylidene, 4-methylbenzylidene, and 2-ethylaminocarbonyl-4-benzylidene.

The Derivatized Antibodies

The derivatized antibodies are intermediates for the synthesis of the conjugates, consisting of the antibody modified by reaction with the linker intermediate. The linker group is terminated with a carbonyl or a di(-methyl or ethyl) acetal thereof, with which the methotrexate drug hydrazide is reacted in a final step. Thus, the X group of the linker terminates with =O or (OCH$_3$)$_2$ or (OCH$_2$CH$_3$)$_2$ in the derivatized antibodies. The carbonyl form is preferred but the acetals are satisfactory reactants and may be used when it is convenient to do so.

The variables X and m have the same values in the derivatized antibodies which have been discussed above. The preferred derivatized antibodies correspond to the preferred conjugates, in that they are comprised of the preferred antibodies, combined with the preferred number m of linker groups made up of the preferred X groups.

Synthesis

The conjugates of the present invention are prepared according to processes which are, in general, similar to those presently used in the art. It is preferred to react the linker with the antibody first, and then to react the linker with the methotrexate drug hydrazide as the final step. An advantage of that synthetic procedure is that the stereospecific form of the methotrexate drug is most readily preserved.

Thus, the first step or steps of the synthesis is to prepare the linker, in an appropriate form to be reacted with the antibody at one end, and with the methotrexate drug at the other. Then, the linker is attached to the antibody to prepare the derivatized antibody, and, finally, the methotrexate drug is attached to the carbonyl or acetal end of the linker. It will be understood that, whenever the antibody is present in a reaction mixture, the process must be carried out under appropriately mild conditions to prevent damage to the antibody.

The synthesis may be represented schematically as follows.

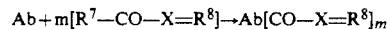

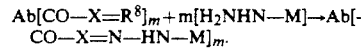

wherein $R^7$ is a carboxylic acid activating group; and Ab, X, $R^8$ and m are as defined above.

In the above formula, the group $R^7$ is chosen from among well-known groups customarily used to activate carboxylic acids for use as acylation reagents. For example, succinimidoxy, phthalimidoxy, methanesulfonyloxy, toluenesulfonyloxy, benzenesulfonyloxy, benzotriazolyloxy, chloro, bromo, azido and the like are commonly used as such activating groups. The preferred activating groups are succinimidoxy, phthalimidoxy and benzotriazolyloxy.

While the reactions are carried out, free amino groups which are part of the pendant $R^1$ substituent are blocked with conventional, readily removed protecting groups. Such groups are exhaustively discussed by Green, Protective Groups in Organic Synthesis, John Wiley & Sons, N.Y., 1981. The groups used here must be removable under quite mild conditions to avoid damage to the antibody. Such protecting groups are known to chemists; particularly useful ones include ethyl acetoacetate, citraconate, and ethyl dimethylmaleate.

The linker intermediates, $R^7$—CO—X=$R^8$, are comparatively simple compounds and can be purchased, or readily prepared by conventional methods. Those linker intermediates having a carboxamido linkage are most conveniently prepared by reacting a primary amine, forming one end of the linker intermediate, with an activated carboxylic acid, forming the other end of the intermediate. Such reactions can be carried out in mild aqueous base at ambient or slightly elevated temperature, and proceed in good yields in a few hours time.

The various steps of the synthesis of the present conjugates can be operated to maximize throughput of the equipment in which the process is carried out, or to maximize yield. In most if not all cases, the antibody itself will represent the largest cost in the process, and therefore optimization of the process will call for maximizing yield based on the antibody. The exact optimum operating conditions, therefore, will depend on the conditions of maximum stability of the particular antibody in use. Accordingly, it is probable that optimum operating conditions will demand the use of quite a large excess of methotrexate drug in order to utilize the antibody to the maximum while minimizing the length of time in which the antibody is exposed to the reaction mixture.

The carboxylic acid activating groups are readily placed on the carboxylic acids of the linker intermediates by use of, for example, dicyclohexylcarbodiimide or other esterification reagents. Such reactions are carried out in inert organic solvents, such as dioxane, tetrahydrofuran, chlorinated hydrocarbons and the like, and may be performed at moderate temperatures in the range of about 0°–50° C. Preparation of the linker intermediates is further explained below in the Preparations.

The primary concern in choosing the conditions under which to react the linker intermediates with the antibody is maintaining the stability of the antibody. The reaction must be carried out in aqueous medium of a composition which will not harm the antibody. A particularly suitable aqueous medium is a borate buffer solution, in which the concentration of borate ion is in the range of about 0.1–0.5 molar. Another appropriate aqueous medium in which to carry out the reaction is physiological buffered saline solution. The pH of the reaction medium should be slightly basic, in the range of about 7–9. While the reaction medium should be aqueous, the presence of small amounts of organic solvents is not harmful, and may be quite convenient. For example, it may be most advantageous to dissolve the linker intermediate in a small amount of organic solvent, for example, dimethylformamide, acetonitrile, tetrahydrofuran, dioxane, or a glycol ether, and add the organic solution to the antibody solution in the aqueous medium.

In general, it will be necessary to operate the reaction at a comparatively low concentration because the solubility of antibodies is generally not great. For example, the concentration of the antibody is usually in the range of about 5–25 mg per ml of aqueous medium.

As described above, from 1 to about 10 moles of linker and drug are attached to each mole of antibody. In order to obtain that conjugation ratio, it is usually necessary to use an excess quantity of linker intermediate. The reactivity of antibodies and active esters under acylating conditions is somewhat variable, but in general, from about 5 to about 15 moles of linker intermediate per mole of antibody are used in the process.

The acylation reaction is allowed to proceed from a few minutes to a few hours, at temperatures in the range from about 0° to about 40° C. Obviously, elevated temperatures may be injurious to the antibody and it is more advisable to operate at low temperatures, particularly since the reaction is inherently quick.

When the derivatized antibody, having the linker intermediate groups in place, has been prepared, the reaction mixture can be chromatographed by conventional procedures, as shown in the examples below, to separate the derivatized antibody from unreacted linker intermediate. If the purification is not done at this point then methotrexate drug will be wasted by reacting it with the excess linker intermediate in the first reaction mixture.

Finally, the drug conjugate is completed by reacting the γ-hydrazide of the methotrexate drug with the derivatized antibody. The reaction is a simple one of the ketone or aldehyde, or acetal thereof, which is the terminating group of the linker intermediate, with the drug hydrazide. It is a quick reaction which goes well at approximately ambient temperature in aqueous media. Ideally, the acylated antibody is purified by chromatography, eluting with a solution which forms a satisfactory reaction medium for the methotrexate drug reaction, as well as providing good separation in the chromatography. Dilute aqueous buffers are appropriate for both purposes.

For example, a particularly useful reaction medium is dilute acetate buffer, more particularly, 0.1 molar sodium acetate at a slightly acid pH in the range of from about 5 to about 7. The reaction also may be carried out, however, in borate buffer, slightly acid phosphate buffers, physiological buffered saline and the like, so long as the pH is slightly acid. Small amounts of organic solvents in the reaction medium are not harmful, as discussed above, so long as the solvents do not have a tendency to damage the antibody.

The reaction with the methotrexate hydrazide is carried out for reaction periods in the range from about an hour to about a day. Reaction temperatures in the range of about 0°–40° C. are used, choosing the temperature to maximize the yield based on the amount of antibody in the reaction mixture.

Finally, the drug conjugate of the present invention is purified and isolated by chromatography by conventional means. It is particularly convenient to elute the drug conjugate with physiological buffered saline. It may be possible to elute the drug conjugate at a concentration which is appropriate for administration to the patient, but it will usually be necessary to concentrate the conjugate, as by vacuum dialysis.

The synthesis of the drug conjugates of the present invention is further explained by the following specific Preparations and Examples.

Preparation 1

Methotrexate-γ-hydrazide

To a 100 ml flask was added 1.61 g (10 mmoles) of L-glutamic acid, 5-methyl ester. To it was added 60 ml of t-butyl acetate and the mixture was stirred briefly. To it was then added, dropwise, 1.58 g (11 mmoles) of 70% perchloric acid, with good stirring. The mixture was allowed to stir under nitrogen for two days, and it was then extracted with 100 ml of 0.5N hydrochloric acid in three portions. The aqueous layers were combined and neutralized with 30 g of sodium bicarbonate. The neutral solution was extracted with three portions of diethyl ether, 150 ml in total, and the organic layers were combined and washed with brine. The washed organic solution was then dried with sodium sulfate and evaporated at ambient temperature under vacuum to obtain 1.18 g (5.4 mmoles) of a clear oil which was identified as L-glutamic acid, 5-methyl-1-t-butyl diester.

To an oven-dried 100 ml flask were added 0.92 ml (6.6 mmoles) of triethylamine, 1 ml (6.6 mmoles) of diethyl cyanophosphonate and 49 ml of dimethylformamide, freshly distilled under vacuum from barium oxide. To the stirred solution was added 506 mg (1.3 mmoles) of 2,4-diamino-6-[N-methyl-N-(4-carboxyphenyl)amino]pteridine trihydrate. When the intermediate had dissolved with stirring, the mixture was heated to 80° C., and then 0.20 ml (1.4 mmoles) of triethylamine and 342 mg of the L-glutamic acid diester prepared above were added in 1 ml of dimethylformamide. The mixture was stirred for two hours at 80° C., and was then cooled and the solvent was removed under vacuum. The residue was taken up in 300 ml of chloroform, and was washed with 5% sodium bicarbonate solution. The aqueous layer was extracted with chloroform, and the organic layers were combined, dried over sodium sulfate, and concentrated under vacuum to obtain 1.35 g of orange oil, which was chromatographed on 150 g of silica gel, eluting with 10% methanol in chloroform. The product-containing fractions were combined and concentrated to obtain 645 mg of methotrexate diester, where the γ-carboxy was in the methyl ester form and the α-carboxy was in the t-butyl ester form.

The above intermediate was combined with another lot of the same, making 697 mg (1.3 mmoles) in all, and was dissolved in 12 ml of methanol. To it was added 170 mg (5.3 mmoles) of anhydrous hydrazine, and the mixture was stirred at ambient temperature under nitrogen for six days. Then the solvent was removed under vacuum, and the residue was chromatographed on 150 g of silica gel, eluting with 15% methanol in chloroform, to obtain 470 mg (0.9 mmoles) of methotrexate-α-t-butyl ester-γ-hydrazide.

The above intermediate was dissolved in 120 ml of 1N hydrochloric acid, and was heated at 55° C. for 50 minutes. It was then concentrated under vacuum to a solid, and the residue was taken up in 80 ml of 0.01M ammonium acetate at pH 8. The solution was stored for three days at 4° C., and was then chromatographed on 300 ml of Sepharose Fast Flow Q, (Pharmacia, Inc., Piscataway, N.J.) eluting in a gradient manner with the same buffer used immediately above (Buffer A) and 1.0M ammonium acetate at pH 8 (Buffer B). The product-containing fractions eluting in 100% Buffer B were combined and repeatedly lyophilized to remove traces of ammonium acetate. The yield was 326 mg (0.7 mmoles) of methotrexate-γ-hydrazide.

Preparation 2

Production of L/1C2 antibodies

Vials of frozen L/1C2 hybridomas are obtained from the American Type Culture Collection, under the accession number HB9682. Viable cells are recovered by thawing the contents of a vial in a 37° C. water bath while swirling the vial. The cell suspension is then diluted 1:2 with balanced salt solution (Grand Island Biological Company (GIBCO), 3175 Staley Road, Grand Island, N.Y. 14072) and the suspension is centrifuged through a serum underlay to partition the cells from the cryogenic medium. The supernatant is aspirated, and the cells in the cell pellet are suspended in culture medium (Ventrex HL-1, Ventrex Laboratories, Portland, Me.) supplemented with 10% fetal calf serum, 2 mM L-glutamine (GIBCO) and 50 ug/ml gentamicin sulfate (GIBCO)) in T75 tissue culture flasks, in 5% carbon dioxide at 37° C. Supernatants from nearly confluent cultures are collected and residual cells are removed by centrifugation. Antibody is purified from the cell free supernatant by passing over a Protein A Sepharose column (Pharmacia). Antibody binds to the column and culture medium is washed free in 0.01M sodium phosphate at pH 8.0. Antibody is then eluted from the column with 0.1M sodium phosphate buffer at pH 3.5. Eluted antibody is immediately neutralized with 1M Trizma buffer (Sigma, St. Louis, Mo.) at pH 7.4 and dialyzed and concentrated in a vacuum dialyzer (Bio-Molecular Dynamics, Beaverton, Oreg.) containing 0.01M sodium phosphate pH 7.4 plus 0.15M sodium chloride. Antibody preparations are sterilized by filtration through 0.2 μm pores and stored at 4° C. until used.

Preparation 3

3-(4-Formylphenylcarbonylamino)propionic acid, N-succinimido ester

To a 250 ml flask were added 3 g (20 mmoles) of 4-carboxybenzaldehyde and 2.3 g (20 mmoles) of N-hydroxysuccinimide in 100 ml of dioxane. The mixture was stirred for 5-10 minutes, and then 4.1 g (20 mmoles) of dicyclohexylcarbodiimide was added. The mixture was stirred for one hour at ambient temperature, and was then filtered. The filtrate was evaporated under vacuum to obtain 9.4 g of a white solid, which was recrystallized from 25 ml of hot isopropanol. The intermediate product was triturated with isopropanol to obtain 2.1 g (8.5 mmoles) of the desired N-succinimido ester of 4-carboxybenzaldehyde.

Additional batches of intermediate were made, and 10 g (40 mmoles) total of the N-succinimido ester was added to a solution of 3.6 g (40 mmoles) of β-alanine in 40 ml of 1N sodium hydroxide and about 100 ml of water. The pH was kept above 8 while the mixture was stirred for 1.5 hours. The mixture was then filtered, and the filtrate was made acid to pH 1.9 with 2N hydrochloric acid. It was extracted three times with 150 ml total of ethyl acetate, and the organic layers were combined and washed with brine. The organic layer was then dried over sodium sulfate and evaporated under vacuum to obtain 4.6 g (21 mmoles) of a white solid, 3-(4-formylphenylcarbonylamino)propionic acid.

One hundred mg (0.45 mmoles) of the above intermediate, 103 mg (0.5 mmoles) of dicyclohexylcarbodiimide, 57.5 mg (0.5 mmoles) of N-hydroxysuccinimide and 10 ml of dioxane were added to a small flask, and the mixture was stirred at ambient temperature under nitrogen. The progress of the reaction was observed by thin layer chromatography, and 75 mg (0.36 mmoles) of additional dicyclohexylcarbodiimide and 45 mg (0.4 mmoles) of additional N-hydroxysuccinimide were added. After four hours, the reaction mixture was filtered, and the filtrate was evaporated to a solid under vacuum. About 200 mg of impure product was obtained, which was chromatographed on 30 g of silica gel, eluting with 5% isopropanol in dichloromethane. The product-containing fractions were combined and evaporated to obtain 81 mg (0.25 mmoles) of the desired intermediate in somewhat impure form.

Preparation 4

Antibody L/1C2 propionyl-3-aminocarbonyl-4-benzaldehyde

To a 100 ml flask at ambient temperature was added a solution of 1026 mg (6.8 μmoles) of antibody L/1C2 in 76.1 ml of 0.34M borate buffer at pH 8.6, followed by 14.1 mg (44 μmoles) of the active ester from Preparation 3, in 3.3 ml of acetonitrile. The mixture was stirred for one hour at ambient temperature. It was then chromatographed on 90 g of Sephadex G25 (Pharmacia), eluting with 0.1M sodium acetate at pH 5.6. The fractions were evaluated by ultraviolet analysis at 258 and 280 nm, and the product-containing fractions were combined to obtain 948 mg (6.3 μmoles) of the desired product, in the form of 111.5 ml of solution having a concentration of 8.5 mg/ml. The conjugation ratio of the derivatized antibody was 4.8 moles of linker per mole of antibody.

animals in each 5-mouse treatment group, which exhibited signs of toxicity. The results were as follows.

TABLE 1

| Treatment | Dose | 14 Days Inhibition | 14 Days Toxicity | 21 Days Inhibition | 21 Days Toxicity | 28 Days Inhibition | 28 Days Toxicity |
|---|---|---|---|---|---|---|---|
| Example 1 | 4 mg/kg | 91% | 3 | 100% | 3 | 100% | 3 |
|  | 2 | 86 | 0 | 98 | 0 | 100 | 0 |
|  | 1 | 94 | 0 | 97 | 0 | 98 | 0 |
|  | 0.5 | 11 | 0 | −27 | 0 | 0 | 0 |
| MTX Hydrazide | 20 | 40 | 0 | 25 | 0 | 14 | 0 |
|  | 4 | 17 | 0 | 5 | 0 | 13 | 0 |
|  | 1 | 11 | 0 | 9 | 0 | 32 | 0 |

EXAMPLE 1

Conjugate of antibody L/1C2 propionyl-3-aminocarbonyl-4-benzaldehyde with methotrexate-γ-hydrazide A 55.6 ml portion of the product of Preparation 4, containing 472 mg (3.1 μmoles) of the derivatized antibody, was diluted with 87 ml of additional 0.1M sodium acetate at pH 5.6.

A 101 mg (216 μmoles) portion of methotrexate-γ-hydrazide was taken up in 7.2 ml of acetonitrile and 21.6 ml of 1M monobasic potassium phosphate buffer. A little 5N sodium hydroxide was added to the solution, and the solution was then added to the antibody solution. The reaction mixture was made acid to pH 5.8 with glacial acetic acid, and was stirred for 16 hours at ambient temperature. It was then centrifuged, and the supernatant chromatographed on two 90 g Sephadex G25 chromatography columns, eluting with physiological buffered saline.

A total of 202.8 ml of solution was collected from the chromatography, which was analyzed by ultraviolet spectroscopy, observing the spectrum at 280 and 370 nm. Analysis showed that the solution contained 0.018 mg/ml of methotrexate, and 1.87 mg/ml of antibody. The conjugation ratio, thus, was 3.0 in molar terms.

The product solution was concentrated by vacuum dialysis against physiological buffered saline in the cold, combining the product solution of this example with 212 ml of product solution from a similar run. The volume was reduced by dialysis to 108 ml.

The product was evaluated against the human tumor T222 (Masui et al., Cancer 44, 1002–07 (1984)), established in female nude mice as xenografts. The conjugate was administered to the mice at the doses (based on content of methotrexate hydrazide) shown in the table below, as intravenous injections, on days 3, 6 and 9 after the tumors were implanted in the mice. The tumors were measured two, three and four weeks after implantation of the tumors, and the results are reported below as the percent inhibition of tumor growth in the treated mice, compared to the growth in untreated control animals. Positive control animals were treated with methotrexate-γ-hydrazide in uncombined form, to provide a comparison with the conjugate-treated animals. Toxicity of the treatments is reported as the number of

EXAMPLE 2

Conjugate of antibody L/1C2 propionyl-3-aminocarbonyl-4-benzaldehyde with methotrexate-γ-hydrazide The process of Example 1 was repeated four times, under different conditions as follows.

A. A 0.67 mg portion of methotrexate-γ-hydrazide, dissolved in 67 μl of 0.1M sodium acetate at pH 5.6 and 33 μl of acetonitrile, was combined with 1 ml of solution containing 2.2 mg of the intermediate of Preparation 4 in 0.1M sodium acetate, and the mixture was allowed to stand for 11 hours. It was then chromatographed on 5.9 g of Biogel P6 (Bio-Rad Laboratories, Richmond, Calif. 94804) to obtain 5 ml of conjugate solution, which was found to contain 0.6 mg of the desired conjugate, at a conjugation ratio of 3.2 moles of methotrexate per mole of antibody.

B. The same amount of methotrexate-γ-hydrazide solution used in A was combined with 0.95 ml of solution of the intermediate of Preparation 4, containing 0.42 mg of the intermediate and the mixture was allowed to stand for 11 hours. It was chromatographed as in A to obtain 4.75 ml of conjugate solution, containing 0.11 mg of conjugate at a conjugation ratio of 5.4 moles per mole.

C. An 0.7 mg portion of methotrexate-γ-hydrazide dissolved in 50 μl of acetonitrile and 100 μl of 1M phosphate buffer at pH 5.8 was combined with 2.2 mg of the intermediate of Preparation 4 dissolved in 1 ml of 0.1M sodium acetate at pH 5.6. When the mixture had stood for 11 hours, it was chromatographed as in A to obtain 5.3 ml of conjugate solution containing 1.3 mg of conjugate at a conjugation ratio of 3.3 moles per mole.

D. An 0.7 mg portion of methotrexate-γ-hydrazide, dissolved in 50 μl of acetonitrile and 150 μl of 1M phosphate buffer at pH 5.8 was combined with 2.2 mg of the intermediate of Example 4, in 1 ml of 0.1M sodium acetate. The mixture was allowed to stand for 14 hours, and was then chromatographed as in A to obtain 5.3 ml of conjugate solution, containing 1.7 mg of conjugate at a conjugation ratio of 3.3.

The products of processes C and D above were evaluated for their ability to inhibit the growth of cells of tumor T222 in tissue culture, by adding controlled concentrations of the conjugates to the culture medium. Free antibody L/1C2, used as a control, inhibited growth of the cells by 37% at 16 mcg/ml, and by 98% at 160 mcg/ml. The conjugate of Example C above inhibited growth by 13% at 0.0013 mcg/ml, and by 87% at 0.013 mcg/ml, based on the content of methotrexate-γ-hydrazide.

The conjugate of Example D above inhibited growth of the cells by 21% at 0.0016 mcg/ml, and by 92% at 0.016 mcg/ml, based on methotrexate-γ-hydrazide content.

Preparation 5

Antibody L/1C2 carbonyl-4-benzaldehyde

A 0.31 mg portion of 4-carboxybenzaldehyde, N-succinimido ester, was prepared as described in Preparation 3 above. It was dissolved in 100 μl of dimethylformamide and was added to 18.9 mg of antibody L/1C2 in 2.1 ml of 0.34M borate buffer at pH 8.6. The mixture was stirred for 1.5 hours at ambient temperature, and it was then chromatographed on 6 g of Biogel P6, eluting with 0.1M sodium acetate at pH 5.6. A 6.2 ml portion of solution was obtained, and was analyzed by ultraviolet, observing the spectrum at 256 and 280 nm. The analysis indicated that 16.1 mg of derivatized antibody was obtained, at a concentration of 2.6 mg/ml, having a conjugation ratio of 5.2 moles of linker per mole of antibody.

EXAMPLE 3

Conjugate of antibody L/1C2 carbonyl-4-benzaldehyde with methotrexate-γ-hydrazide Four ml of the solution from Preparation 5, containing 10.4 mg (0.069 μmoles) of derivatized antibody, was combined with 3.2 mg (6.8 μmoles) of methotrexate-γ-hydrazide in 250 μl of dimethylformamide. The mixture was allowed to stand for 6 hours at ambient temperature, and was then placed in the refrigerator. After two days, the mixture was centrifuged, and the supernatant was chromatographed on Bio-Gel P6, eluting with physiological buffered saline, to obtain 8.5 ml of solution, which was analyzed by ultraviolet, observing the spectrum at 280 and 370 nm. The analysis showed that the product had a conjugation ratio of 6.4 moles of drug per mole of antibody, and that the solution contained 0.64 mg/ml of conjugate.

The product was evaluated for its ability to inhibit the growth of T222 tumor cells in tissue culture. It was found that the conjugate produced 70% inhibition of cell growth at 0.035 mcg/ml concentration, based on methotrexate content.

Preparation 6

Antibody L/1C2 F(ab')2 fragment

The F(ab')2 fragment of antibody L/1C2 was prepared by adding 2.4 ml of pepsin solution, containing 12.6 mg of pepsin/ml, to 1.5 g of L/1C2 antibody in 270 ml of physiological buffered saline. The mixture was held at 37° C. for 2 hours and 20 minutes, and then the reaction was stopped by the addition of triethanolamine. The product was then concentrated by chromatography on a Sepharose Fast Flow column, eluting with 0.15M sodium acetate. The F(ab')2 -containing fractions were combined, and concentrated by dialysis to obtain 100 ml of product solution containing 992 mg of the F(ab')2 fragment of antibody L/1C2.

Preparation 7

Antibody L/1C2 F(ab')2 fragment propionyl-3-aminocarbonyl-4-benzaldehyde

L/1C2 F(ab')2 fragment, prepared in Preparation 6, was dialyzed into 0.34M borate buffer at pH 8.6 to obtain 23 mg (0.23 μmoles) of F(ab')2 fragment in the form of 3.8 ml of solution. That solution was combined with 0.44 mg (1.4 μmoles) of 3-(4-formylphenylcarbonylamino)propionic acid, N-succinimido ester, in 102 μl of acetonitrile. The mixture was stirred for one hour at ambient temperature, and the solution was then chromatographed over a column of 11 g of Sephadex G25, eluting with 0.1M sodium acetate at pH 5.6. The product-containing fractions were combined to obtain 19 mg (0.19 μmoles) of derivatized antibody fragment, at a conjugation ratio of 2.8 moles per mole, in 9.6 ml of solution.

EXAMPLE 4

Conjugate of L/1C2 F(ab')2 fragment propionyl-3-aminocarbonyl-4-benzaldehyde with methotrexate-γ-hydrazide To 2.7 ml of the derivatized antibody fragment solution from Preparation 7, containing 8 mg (0.08 μmoles) of derivatized antibody fragment, was added 0.47 ml of 1M phosphate buffer at pH 5.6. To that solution was added 3.7 mg (7.g μmoles) of methotrexate-γ-hydrazide, dissolved in the minimal amount of 0.1M sodium acetate. The pH of the mixture was adjusted back to 5.6 with dilute hydrochloric acid, and the mixture was stirred for 17 hours at ambient temperature. It was then centrifuged, and the supernatant was chromatographed on a column of 11 g of Sephadex G25, eluting with physiological buffered saline. Ultraviolet analysis showed that 5.8 mg of conjugate was obtained, in the form of a solution containing 0.95 mg/ml, at a conjugation ratio of 2.1 moles per mole.

The conjugate was tested in tissue culture against T222 tumor cells, and was found to inhibit growth of the cells to the extent of 22% at a concentration of 0.0046 mcg/ml, and to inhibit growth by 83% at a concentration of 0.046 mcg/ml, based on content of methotrexate-γ-hydrazide.

Preparation 8

3-(5-Formylpyrrol-2-ylcarbonylamino)propionic acid, N-succinimido ester

To a flask were added 139 mg of 5-formylpyrrol-2-ylcarboxylic acid, 247 mg of dicyclohexylcarbodiimide, 138 mg of N-hydroxysuccinimide and 10 ml of dimethylformamide. The mixture was stirred for two hours at ambient temperature under nitrogen, and the solvent was removed under vacuum to obtain 394 mg of crude active ester.

The above residue was taken up in 1 ml of acetonitrile. Not all of the residue went into solution. The heterogeneous mixture was added slowly to a solution of 89 mg of β-alanine in 2 ml of 0.5N sodium hydroxide. Concurrently, 1N sodium hydroxide was added to maintain the pH between 7.5 and 8.0. The mixture was then stirred at ambient temperature for 1 hour, and was filtered. The filtrate was made acid with dilute hydrochloric acid, was saturated with sodium chloride, and was extracted with ethyl acetate. It was then dried and concentrated to an orange oil, which was chromatographed on a silica gel column, eluting with 10% methanol in dichloromethane. The product-containing fractions were concentrated under vacuum to obtain 49 mg of 3-(5-formylpyrrol-2-ylcarbonylamino)propionic acid.

A 31 mg portion of the above intermediate was taken up in 3 ml of dioxane, and to it was added 35 mg of dicyclohexylcarbodiimide and 19 mg of N-hydroxysuccinimide. The mixture was stirred for 2 hours at ambient temperature under nitrogen, and was then filtered and concentrated under vacuum. The residue was chromatographed on silica gel, eluting with 5% methanol in dichloromethane to obtain about 6 mg of the desired intermediate active ester.

Preparation 9

Antibody 007B propionyl-3-aminocarbonyl-2-pyrrol-5-carboxaldehyde

Antibody 007B is produced by a hybridoma which is a subclone derived from the hybridoma producing the antibody KS1/4, which was described by Varki et al., *Cancer Research* 44, 681–86 (1984). A 105 mg portion of antibody 007B, in the form of a solution containing 15 mg/ml in 0.34M borate buffer, was combined with 300 µl of a solution of the intermediate of Preparation 8 containing 1.29 mg of the intermediate active ester in acetonitrile. The mixture was stirred for 1 hour at ambient temperature, and was then chromatographed over a 10 g column of Sephadex G25, eluting with 0.1M sodium acetate at pH 5.6. The product-containing fractions were combined and analyzed by ultraviolet spectroscopy, observing the curve at 280 and 300 nm. The product comprised 14.6 ml of solution, at a concentration of 5.7 mg/ml, a total of 83.2 mg of the intermediate named above. The conjugation ratio was 3.6.

EXAMPLE 5

Conjugate of antibody 007B propionyl-3-aminocarbonyl-2-pyrrol-5-carboxaldehyde with methotrexate-γ-hydrazide A 15 mg portion of the intermediate of Preparation 9, in the form of 3.1 ml of a solution containing 4.8 mg/ml of a buffer at pH 5.6 containing 0.1M sodium acetate and 0.15M phosphate ion, was combined with 4.7 mg of methotrexate-γ-hydrazide in 0.2 ml of sodium acetate buffer. The pH was adjusted to 5.6 after the addition, and the mixture was stirred at ambient temperature for about 24 hours. It was then centrifuged, and the supernatant was chromatographed on a 10 g column of Sephadex G25, eluting with physiological buffered saline. The product-containing fractions were combined and filtered through an 0.22 micron filter to obtain 6.05 ml of product solution containing 9.9 mg of the desired conjugate, at a conjugation ratio of 2.3, as determined by ultraviolet spectroscopy, observing the curve at 250 and 280 nm. The binding capacity of the conjugate was assessed by radioimmunoassay, comparing it with unconjugated 007B antibody. The titration curves of the conjugate and the antibody were substantially similar, indicating that the binding capacity of the antibody was essentially unchanged by conjugation with the linker and drug.

Preparation 10

Antibody KS1/4 propionyl-3-aminocarbonylbutanal, diethylacetal

Antibody KS1/4 was dialyzed into 0.34M borate buffer at pH 8.6, at a concentration of 20 mg/ml. One ml portions of the antibody solution were reacted with 3-(4,4-diethoxybutylaminocarbonyl)propionic acid, N-succinimido ester, which was added as a 20 mg/ml solution in dimethylformamide. In one case the amount of active ester was 0.24 mg, and in the other case the amount was 0.48 mg. Both reaction mixtures were stirred for 2 hours, and were then chromatographed over Biogel P6, eluting with physiological buffered saline.

The product of the first reaction was 17.8 mg of the desired intermediate, and the product of the second reaction was 15.6 mg of the desired intermediate.

EXAMPLE 6

Conjugate of antibody KS1/4 propionyl-3-aminocarbonylbutanal, diethylacetal with methotrexate-γ-hydrazide One ml portions of the derivatized antibody made in Preparation 10 above were reacted with methotrexate-γ-hydrazide in 0.34M borate buffer at pH 8.6. In the case of the first product of Preparation 10, 3.5 mg of the product above was reacted with 2.3 mg of methotrexate-γ-hydrazide as a dimethylformamide solution. In the case of the second product, the amount of it was 2.9 mg and the amount of methotrexate-γ-hydrazide was 2.0 mg. In each case the reaction mixture was then adjusted to pH 4.9. The reactions were then carried out for 18 hours at 37°, and the products were chromatographed on Biogel P6, eluting with physiological buffered saline.

The product-containing fractions of each reaction were combined, and were analyzed by ultraviolet spectroscopy, observing the curves at 279 and 370 nm. The product of the first reaction was 2.7 mg of the desired conjugate, at a conjugation ratio of 2.0. The product of the second reaction was 2.6 mg, at a conjugation ratio of 3.9.

The conjugates of the present invention are useful in the method of inhibiting the growth of unwanted cells which is an important part of the present invention. Accordingly, the invention also includes a pharmaceutical composition, most preferably a parenteral composition suitable for injection into the body of the patient. Such compositions are formulated by methods which are commonly used in pharmaceutical chemistry. The present conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as lactose, to allow the dried preparation to dissolve quickly upon reconstitution. Such formulations are reconstituted with highly purified water to a known concentration, based on the methotrexate drug.

The optimum dosage and administration schedule of conjugates of the present invention must be determined by the treating physician, in the light of the patient's condition.

It is customary, of course, to administer cytotoxic drugs in the form of divided doses, with intervals of days or weeks between each series of doses. The present conjugates are effective over a wide dosage range, and dosages per week will usually fall within the range from about 50 to about 1000 mg/m$^2$ of methotrexate drug, more preferably in the range from about 200 to about 400 mg/m$^2$.

We claim:

1. A derivatized antibody of the formula

Ab[CO—X=R⁸]ₘ wherein m is an integer from 1 to about 10;

R⁸ is O, (OCH₃)₂ or (OCH₂CH₃)₂;

Ab is a physiologically-acceptable antibody or antigen-recognizing fragment thereof, which recognizes an antigen associated with an undesirable cell;

X is a linker of the formula

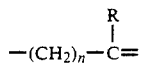

—(CH₂)ₙAr—CH=

—(CH₂)ₙ—CO—NH—(CH₂)ₙ—CH= or

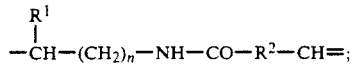

R is hydrogen, phenyl, or phenyl substituted with one or two nitro, halogen, cyano or trifluoromethyl groups;

Ar is

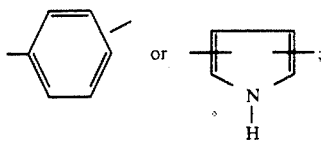

R¹ is hydrogen, amino, amino-C₁-C₄ alkyl, hydroxy-C₁-C₄ alkyl, or guanidino-C₁-C₄ alkyl;

R² is (CH₂)ₙ'

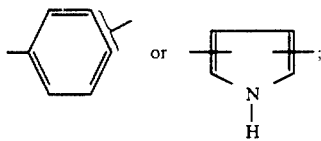

n is an integer from 0 to 5 provided when X is —(CH₂)ₙ—Ar—C= and Ar is

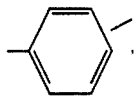

n may not be 0.

2. A derivatized antibody of claim 1 wherein the antibody is a monoclonal or chimeric antibody, or an antigen-recognizing fragment thereof.

3. A derivatized antibody of claim 2 wherein X is

—(CH₂)ₙ—Ar—CH=.

4. A derivatized antibody of claim 3 wherein m is from about 3 to about 8.

5. A derivatized antibody of claim 4 wherein the antibody is L/1C2.

* * * * *